United States Patent [19]

Widauer

[11] Patent Number: 5,534,505
[45] Date of Patent: Jul. 9, 1996

[54] URSODEOXYCHOLIC ACID-CONTAINING MEDICAMENT IN A LIQUID ADMINSTRATION FORM

[75] Inventor: Josef O. Widauer, Allschwil, Switzerland

[73] Assignee: Medichemie AG, Bruhlstrasse, Switzerland

[21] Appl. No.: 296,355

[22] Filed: Aug. 25, 1994

[30] Foreign Application Priority Data

Aug. 30, 1993 [CH] Switzerland ............................. 2567/93

[51] Int. Cl.$^6$ .................................................. A61K 31/56
[52] U.S. Cl. .......................... 514/169; 514/937; 514/944; 514/951; 514/974
[58] Field of Search .................................. 514/169, 937, 514/944, 951, 974

[56] References Cited

U.S. PATENT DOCUMENTS

| | | | |
|---|---|---|---|
| 3,639,597 | 2/1972 | Hannah | 424/238 |
| 4,242,360 | 12/1980 | Pailer et al. | 424/343 |
| 4,264,583 | 4/1981 | Jandacek | 424/240 |
| 5,302,398 | 4/1994 | Egidio et al. | 424/474 |

FOREIGN PATENT DOCUMENTS

| | | | |
|---|---|---|---|
| 1904562A | 3/1970 | Germany . | |
| 55-022616 | 2/1980 | Japan | C07J 9/00 |
| 62-153220 | 7/1987 | Japan | A61K 31/575 |

*Primary Examiner*—José G. Dees
*Assistant Examiner*—Rosalynd A. Williams
*Attorney, Agent, or Firm*—Tarolli, Sundheim, Covell, Tummino & Szabo

[57] ABSTRACT

The active agent ursodeoxycholic acid has proved therapeutically active in infants, inter alia for the treatment of cholestatic hepatic diseases. A problem when administering this active agent, a bile acid, to infants is its extreme bitterness. As a result of the present invention a taste-acceptable, liquid administration form for ursodeoxycholic acid with an adequately high active agent concentration is described. The liquid to be ingested is a suspension prepared accompanied by the addition of a swelling and/or thickening agent, which contains the active agent mainly in fine crystalline form as the disperse phase and only in a much smaller proportion dissolved in the aqueous dispersant. A remaining residual bitterness can be additionally masked by the addition of β-cyclodextrin or suitable taste correcting agents.

10 Claims, No Drawings

URSODEOXYCHOLIC ACID-CONTAINING MEDICAMENT IN A LIQUID ADMINSTRATION FORM

TECHNICAL FIELD

The present invention relates to a ursodeoxycholic acid-containing medicament in a liquid administration form, particularly for the treatment of cholestatic hepatic diseases in infants.

The human bile pool contains different bile acids, including normally up to 70 to 80% chenodeoxycholic acid and up to approximately 3% of ursodeoxycholic acid. In the cholestase syndrome due to an inadequate or no outflow of bile into the intestine there is a back-flow of bile fluid into the liver and damage to the liver cells, particularly as a result of the aggressive chenodeoxycholic acid. However, as a result of the planned administration of ursodeoxycholic acid it is possible to modify the ratio of the two bile acids in the bile acid pool strongly in favour of the much less aggressive ursodeoxycholic acid and consequently bring about a significant overall reduction in the aggressiveness of the bile liquid.

PRIOR ART

All bile acids, including ursodeoxycholic acid, have an extremely bitter taste and an equally bitter after-taste lasting several hours. With the standard oral administration in the form of capsules or tablets it is admittedly possible to effectively conceal the bitter taste, but these administration forms are scarcely usable particularly in pediatrics, because infants cannot or can only with difficulty swallow capsules or tablets. In pediatrics preference is given to liquid administration forms, particularly in view of the fact that in the case of infants they can be better dosed in accordance with the body weight. Also in the case of liquid administration forms taste masking or concealing is possible, e.g. through the use of pellets. Pellets are small balls in which the active agent is enclosed and is consequently not in direct contact with the oral mucosa. The pellets are administered dispersed in suspensions. However, the production of pellets is complicated and expensive. They are very fragile, so that there is a risk of them being broken or bitten. In addition, it is generally only possible to have relatively small active agent quantities in each weight unit. In the case of ursodeoxycholic acid it is possible in this way to obtain a concentration of 20 to 30 mg/ml, whereas a concentration of approximately 50 mg/ml would be desirable. In order to be able to administer the ursodeoxycholic acid in a sufficiently high dosage (15 to 20 mg/kg of body weight and day), up to now there has been no taste masking in practice and instead a solution of the bile acid has been prepared in sodium bicarbonate, which has been administered by probe.

DESCRIPTION OF THE INVENTION

The problem of the present invention is to provide a taste-acceptable, liquid administration form for ursodeoxycholic acid with an adequately high active agent concentration. According to the invention this problem is solved in that the liquid to be ingested is a suspension prepared with the addition of a swelling and/or thickening agent, which contains the active agent mainly in a fine crystalline form as the disperse phase and only in a much smaller proportion dissolved in the aqueous dispersant.

The ursodeoxycholic acid formulation given by the invention has a comparatively very small residual bitterness. The strong reduction of the extremely bitter taste of the bile acid can probably be attributed to the fact that the fine acid crystals (particle size preferably over 99%<90 µm) are individually enclosed and enveloped by the swelling or thickening agent. On ingesting the liquid the acid crystals consequently do not or only to a limited extent come into direct contact with the oral mucosa. Although such taste masking phenomena are known per se, the extent to which it is possible to reduce the bitterness of the bile acid in the present case is surprising and unexpected. The still present residual bitterness is mainly caused by the active substance proportion dissolved in the dispersant. The embedding of the acid crystals in the swelling or thickening agent has a favourable action by making the dissolving thereof in the dispersant more difficult. Thus, in the case of 50 mg/ml of active agent, the dissolved active agent proportion is only approximately 0.5%.

The dispersant is preferably demineralized water. As the swelling or thickening agent it is possible to use various substances including e.g. aluminosilicate, bentonite or different forms of methyl cellulose, hydroxypropyl methyl cellulose, hydroxypropyl cellulose, hydroxyethyl cellulose and gallactomannas. In view of the long-term stability of the suspension and its flow characteristics (viscosity, thixotropy) it has proved particularly appropriate to use a microcrystalline cellulose, which is dispersible in water and which is offered for sale under the trademark AVICEL® RC 591 by FMC Corporation, Philadelphia, U.S.A. It contains a proportion of sodium carboxymethyl cellulose as the protective colloid. Other swelling agents supplied by the same company under the name AVICEL® are also fundamentally usable.

The particularly appropriate active substance concentration is 50 mg/ml. However, it is also possible to prepare suspensions with possibly necessary other active agent concentrations (e.g. only 25 mg/ml or up to 75 mg/ml).

The residual bitterness produced by the dissolved active agent proportion can be further reduced by adding β-cyclodextrin, which is a ring-shaped molecule built up from seven glucose units. The ring interior is hydrophobic and is able to bind a hydrophobic molecule. The ring exterior is hydrophilic and compatible with the aqueous dispersant. The cyclodextrin forms with the dissolved active agent an inclusion compound, in that the active agent molecule is enclosed as a "guest" in the cyclodextrin "host" molecule. Thus, there is once again a spatial shielding of the active agent molecule.

The suspension according to the invention can also be mixed with preservatives and for further taste improvement purposes with sweeteners as well as flavouring agents and sodium chloride.

The pH-value also plays an important part with regards to the bitterness. The active agent dissolves, accompanied by salt formation, with rising pH and therefore intensifies the bitterness. It is therefore advantageous to adjust the pH-value of the suspension to between 2.5 and 8, preferably 3.5 and 6 by using suitable buffer systems (e.g. phosphate or citrate buffer, e.g. McIlvaine buffer).

EXAMPLES

Hereinafter is given a preferred composition for 1 ml of the suspension according to the invention. The values in brackets give the possible variation range quantities for the individual components, the in each case smallest values being used with the smallest active agent quantity given and the in each case largest values with the largest active agent quantity given.

| Component | Quantity (g) | Function |
|---|---|---|
| fine ursodeoxycholic acid | 0.05 (0.025–0.075) | active agent |
| β-cyclodextrin | 0.1 (0.015–0.3) | taste masker |
| AVICEL ® RC 591 | 0.01 (0.005–0.03) | thickener |
| saccharose | 0.3 (0.15–0.45) | sweetener |
| methylparaben | 0.0013 (0.0012–0.0014) | preservative |
| propylparaben | 0.0002 (0.0001–0.0003) | preservative |
| propylene glycol | 0.05 (0.045–0.055) | solubilizer for preservatives |
| flavouring agents | 0.0013 (0.001–0.0015) | |
| demineralized water | ad 1.00 ml | dispersant | or in the sugar-free form:

| Component | Quantity (g) | Function |
|---|---|---|
| fine ursodeoxycholic acid | 0.05 | active agent |
| hydroxyethyl cellulose | 0.008 (0.004–0.012) | thickener |
| benzoic acid | 0.0015 | preservative |
| xylitol | 0.32 (0.25–0.4) | sweetener |
| glycerol | 0.1 (0.05–0.2) | sweetener |
| sodium cyclamate | 0.005 | sweetener |
| sodium chloride | 0.0007 (0.0005–0.002) | taste masker |
| citric acid | 0.002 | buffer |
| sodium citrate | 0.0014 | buffer |
| flavouring agents | 0.0005 | |
| purified water | ad 1.0 (ml) | |

The preparation of a suspension in one of the above compositions preferably takes place in the following stages:

Methyl and propylparaben are completely dissolved in propylene glycol in a container, accompanied by stirring and at approximately 70° C. and allowed to cool.

The water is placed in a container and the AVICEL® RC591 is dispersed therein with a high-speed homogenizing rod.

By means of the homogenizing rod the active agent ursodeoxycholic acid and β-cyclodextrin are successively incorporated portionwise therein.

The paraben solution is added.

The saccharose is incorporated by means of the homogenizing rod.

After allowing to stand for several hours the flavouring agent is added and the resulting suspension is again briefly homogenized.

The preparation of a suspension according to the invention without β-cyclodextrin preferably takes place as follows:

The methyl and propylparaben are completely dissolved in propylene glycol in a container, accompanied by stirring at approximately 70° C. and allowed to cool.

The saccharose is dissolved in ⅔ of the water in a container, accompanied by stirring at ambient temperature.

Using a high-speed homogenizing rod the AVICEL® RC591 is incorporated into ⅓ of the water in a container and the paraben solution and saccharose solution are added to the AVICEL® RC591 dispersion.

The active agent ursodeoxycholic acid is incorporated in several portions by means of the homogenizing rod.

The flavouring agent is added and the resulting suspension is again briefly homogenized.

The preparation of the suspension according to the invention, without sugar, preferably takes place in the following way:

The hydroxyethyl cellulose is dissolved in ⅔ water, accompanied by stirring and at approximately 40° C.

The benzoic acid, xylitol, sodium cyclamate, sodium chloride, citric acid and sodium citrate are dissolved in the hydroxyethyl cellulose solution.

The glycerol is mixed with ⅓ water and into it is incorporated at ambient temperature and by means of the homogenizing rod the ursodeoxycholic acid.

The ursodeoxycholic acid suspension is incorporated, accompanied by stirring, into the hydroxyethyl cellulose solution.

The flavouring agents are added, accompanied by stirring.

I claim:

1. Medicament in a liquid administration form containing ursodeoxycholic acid as the active agent, particularly for the treatment of cholestatic hepatic diseases in infants, characterized in that the liquid to be taken is a suspension prepared by the addition of a swelling or thickening agent which said suspension contains the active agent mainly in a finely crystalline form in the disperse phase and only in a much smaller proportion dissolved in the aqueous dispersant.

2. Medicament according to claim 1, characterized in that over 99% of the fine crystalline active agent has a nucleus size smaller than 90 μm.

3. Medicament according to claim 1, characterized in that demineralized water is used as the aqueous dispersant.

4. Medicament according to claim 1, characterized in that the swelling or thickening agent is a microcrystalline cellulose, which is dispersible in water and which contains a proportion of sodium carboxymethyl cellulose as a protective colloid and is present in a quantity range of 0.005 to 0.03 g/ml.

5. Medicament according to claim 1, characterized in that the suspension additionally contains β-cyclodextrin as a taste masking agent for the active agent dissolved in the dispersant.

6. Medicament according to claim 1, characterized in that the suspension additionally contains as preservatives methylparaben and/or propylparaben and/or benzoic acid.

7. Medicament according to claim 6, characterized in that the suspension additionally contains propylene glycol as a solubilizer for the preservatives.

8. Medicament according to claim 1, characterized in that the suspension additionally contains saccharose as a sweetener and/or flavoring agents.

9. Medicament according to claim 1, characterized in that the suspension contains a sugar substitute.

10. Medicament according to claim 1, characterized in that the suspension has a pH-value adjusted to between 2.5 and 8.

* * * * *